US009146219B2

(12) United States Patent
Yue et al.

(10) Patent No.: US 9,146,219 B2
(45) Date of Patent: Sep. 29, 2015

(54) SENSITIVE METHOD FOR MEASURING CIS-DIOL CONTAINING COMPOUNDS IN PLASMA USING 2D-LC-MS/MS

(71) Applicant: National Medical Services, Inc., Willow Grove, PA (US)

(72) Inventors: Bingfang Yue, North Wales, PA (US); Shuguang Li, Abington, PA (US); Wenzhe Li, Middletown, DE (US)

(*) Notice: Subject to any disclaimer, the term of this patent is extended or adjusted under 35 U.S.C. 154(b) by 0 days.

(21) Appl. No.: 14/605,617

(22) Filed: Jan. 26, 2015

(65) Prior Publication Data
US 2015/0212055 A1    Jul. 30, 2015

Related U.S. Application Data

(60) Provisional application No. 61/932,137, filed on Jan. 27, 2014.

(51) Int. Cl.
| | | |
|---|---|---|
| G01N 33/58 | (2006.01) | |
| G01N 33/567 | (2006.01) | |
| G01N 30/72 | (2006.01) | |
| H01J 49/00 | (2006.01) | |

(52) U.S. Cl.
CPC .......... *G01N 30/7233* (2013.01); *H01J 49/004* (2013.01)

(58) Field of Classification Search
CPC ............ C12Q 1/6872; G01N 33/6848; G01N 33/6821; G01N 33/597; G01N 33/58
USPC .......... 250/282; 435/7.1, 23, 4; 436/518, 514, 436/8, 86
See application file for complete search history.

(56) References Cited

U.S. PATENT DOCUMENTS

| | | | | |
|---|---|---|---|---|
| 6,162,926 A * | 12/2000 | Murphy et al. | ............... | 548/417 |
| 6,312,893 B1* | 11/2001 | Van Ness et al. | ............. | 435/6.12 |
| 6,949,347 B2* | 9/2005 | Singh et al. | .................... | 435/7.1 |
| 9,023,656 B2* | 5/2015 | Hamon et al. | ................ | 436/173 |
| 2005/0042676 A1* | 2/2005 | Hamon et al. | ................. | 435/7.1 |
| 2005/0095661 A1* | 5/2005 | Hamon et al. | .................. | 435/23 |
| 2011/0282587 A1* | 11/2011 | Jones et al. | ..................... | 702/19 |

* cited by examiner

*Primary Examiner* — David A Vanore
(74) *Attorney, Agent, or Firm* — Joseph F. Aceto, Esq.

(57) ABSTRACT

The present invention provides methods for determining the amount of cis-diol containing compounds in a biological samples using mass spectrometry, particularly catecholamines (dopamine, epinephrine, norepinephrine) in a plasma sample. After a sample is mixed with an internal standard, extracted with a two-step liquid-liquid extraction process utilizing phenylboronic acid chemistry, and then derivatized with a benzoyl chloride-like agent, relevant moieties are then separated chromatographically and detected by MS/MS whereby specific ion transitions are monitored. This invention has several clinical utilities, particularly those related to measuring plasma catecholamines in patients.

20 Claims, 10 Drawing Sheets

Dopamine (DA)
*log $D_{pH\ 3}$ −2.8
*p$K_{a\ NH2}$ 8.8
M = 153

Noradrenaline (NA)
log $D_{pH\ 3}$ −4.0
p$K_{a\ NH2}$ 8.5
M = 169

Adrenaline (A)
log $D_{pH\ 3}$ −3.5
p$K_{a\ NH2}$ 8.4
M = 183

Panel A

Panel B

Panel C

Panel A

Panel B

Panel C

Panel A

Panel B

Panel C

SENSITIVE METHOD FOR MEASURING CIS-DIOL CONTAINING COMPOUNDS IN PLASMA USING 2D-LC-MS/MS

CROSS-REFERENCE TO RELATED APPLICATIONS

This application claims the benefit of U.S. Provisional Application No. 61/932,137, filed Jan. 27, 2014 and incorporated by reference in its entirety.

BACKGROUND

1. Field of Invention

The present invention relates to analytical methods for the detection of cis-diol containing compounds including catecholamines. More specifically, the present invention provides a quantitative assay for detecting dopamine, epinephrine or norepinephrine in plasma of individuals using mass spectrometry.

2. Description

Catecholamines (dopamine, norepinephrine/noradrenaline, and epinephrine/adrenaline) act as neurotransmitters or hormones at both central and peripheral levels, in both neuronal and non-neuronal tissues. The involvement of catecholamines in multiple regulatory systems and metabolic processes supports their important role as biomarkers for the clinical diagnosis, therapy, and prognosis of several neuroendocrine and cardiovascular disorders.

Tyrosine is the amino acid precursor of catecholamines which produces L-dihydroxylphenyl alanine (L-DOPA) through the action of tyrosine hydroxylase. In the central nervous system the activity of decarboxylase activity with L-DOPA produces dopamine and norepinephrine which act as neurotransmitters. The adrenal medulla produces both epinephrine and norepinephrine (via dopamine β-hydroxylase). The neurons release norepinephrine through postganglionic sympathetic nerves. Conversion of norepinephrine to epinephrine occurs mainly in the adrenal medulla through the activity of N-methyl transferase. FIG. 1 provides the molecular structure and physiochemical properties for dopamine, noradrenaline, and adrenaline.

When catecholamines are released from the sympathetic tissue, other than the adrenal medulla, the primary means of physiologic inactivation is the return of unaltered catecholamines by an active transport mechanism. The residual hormone may then be metabolized or excreted unchanged by the kidney.

When metabolized, two enzymes are important, monamine oxidase (MAO) which is responsible for oxidative deamination and catechol-O-methyltransferase (COMT), which is responsible for O-methylation. COMT is principally responsible for inactivating circulating catecholamines, whereas MAO is thought to play a role in disposing of excess catecholamine stores. The major end product for metabolism of epinephrine or norepinephrine is 3-methoxy-4-hydroxymandelic acid (VMA). Other urinary metabolites of catecholamines are metanephrine and normetanephrine.

Catecholamines have very low molecular weights and are extremely low concentration in biological samples. Analysis of catecholamines in biological sample is prone to a lot of potential interference present in biological matrix. Catecholamines are extremely polar and very weakly retained chromatographically in commonly used reverse phase liquid chromatography. Catecholamines are chemically unstable, prone to spontaneous oxidation and decompose easily at high pH. Catecholamines chelate quickly to multivalent cation such as iron, copper, etc. in solution. Catecholamines adsorb strongly to various contact surfaces such as glass and metal by complex formation, including fluidic path in the LC-MS/MS system, leading to significant absorption loss. The measurement of catecholamines in biological samples remains a current analytical challenge, in spite of the great diversity of methodologies that have been developed throughout the years. The quantification of catecholamines in biological samples demands specific and very sensitive bioanalytical methods.

Current standard method of choice is high performance liquid chromatography (HPLC) with electrochemical (ECD) detection, despite time consuming sample preparation, long chromatographic runtime (approximately 30 minutes), prone to various interferences, and low sensitivity, severely limiting its clinical use. Other methods include fluorometric assays, radio enzymatic assays (REA), gas chromatography with mass spectrometric detection (GC-MS), radio immunoassays (RIA) and enzyme immunoassays (EIA). Fluorometric and radio enzymatic assays lack accuracy and reproducibility and the fluorometric assays do not differentiate between different catecholamines. HPLC and GC-MS are time consuming, need complex technical equipment and, therefore, are cost-intensive, leaving any suitable methods for determining catecholamines based on reliability, cost, accuracy, reproducibility and rapidness to be immunoassays.

In currently available EIA or RIA based assays for determining catecholamines, the catecholamines are first extracted out of the sample, then derivatized for antibody recognition and to enhance their stability, and thereafter detected using antibodies specific for catecholamines. Consequently, the most commonly used extraction method is binding of the catecholamines via their cis-diol structure to a boronate affinity gel (Cannizzo C. et al., 2005 Polymer 46, 1269-1276). The subsequent modification to stabilize the catecholamines is done using the enzyme catechol-O-methyl-transferase (COMT) which O-methylates the 3-hydroxyl group of the catechol moiety. For the COMT to access the 4-hydroxyl group of the catechol moiety, the catecholamines have to be released from the affinity gel which is achieved by adjusting the pH to acidic conditions. However, COMT is not active under acidic conditions. Therefore, in order to allow the reaction catalyzed by COMT to take place and prevent rebinding of the catecholamines released from the boronate affinity gel, the released catecholamines have to be separated from the boronate affinity gel by transferring them into another reaction vessel. This transfer of the sample creates an additional source of error and complicates the assay.

One means for reducing the transfer steps in methods for analyzing catecholamines by EIA is to perform the enzymatic O-methylation and the subsequent EIA in one reaction vessel. However because derivatization of the catecholamines and binding to the specific antibodies proceed in a parallel manner and since only derivatized catecholamines are detected by the antibodies, the results and kinetics of the EIA are less precise. Further, this method cannot be performed in standard automated EIA analyzer due to the preceding enzymatic reaction taking place in the same reaction vessel.

The assay of the present invention provides a simple, fast, and sensitive 2D-LC-MS/MS method to measure three catecholamines (dopamine, norepinephrine, and epinephrine) in a routine clinical laboratory setting.

SUMMARY

The present invention is directed to meeting the foregoing needs by providing a simple and convenient method of assaying catecholamines in plasma. The method incorporates the detection of epinephrine, norepinephrine, and dopamine in a biological sample by mass spectrometry, including tandem mass spectrometry. Accordingly a sensitive and specific method is described that accurately quantifies three catecholamines in heparin plasma by 2D-LC-MS/MS. The prior methods are disadvantageous at least because they do not measure dopamine, norepinephrine, and norepinephrine in a consistent and reproducible method, suitable for clinical use. Further, prior methods require the steps of transferring the sample in a different reaction vessel to avoid rebinding of catecholamines to the cis-diol specific affinity medium used for extraction of the catecholamines from the sample. Thus, a need has arisen for a simple and effective way to measure the status of these compounds.

The present invention involves a novel procedure that allows quantification of dopamine, norepinephrine, and norepinephrine from plasma using mass spectrometry. One advantage of the method is that it is capable of measuring dopamine, norepinephrine, and norepinephrine from plasma quickly and reproducibly by 2D-LC-MS/MS after sample preparation that includes a two-step liquid-liquid extraction specific for compounds containing cis-diol (catechol) groups, using phenylboronic acid and tetraoctylammonium bromide.

Accordingly in a preferred embodiment, methods are provided for determining the amount of dopamine, norepinephrine, and/or epinephrine in a plasma sample by tandem mass spectrometry that include: (a) spiking a heparin plasma sample with an internal standard; (b) extracting with a two-step liquid-liquid extraction specific for compounds containing catechol groups; (d) derivatizing the cis-diol containing compounds with benzoyl chloride; and (e) identifying and quantitating by 2D-LC-MS/MS.

The methods of the invention may be used in health maintenance, disease prevention, and general patient monitoring.

DETAILED DESCRIPTION

Definitions

Figure 1:
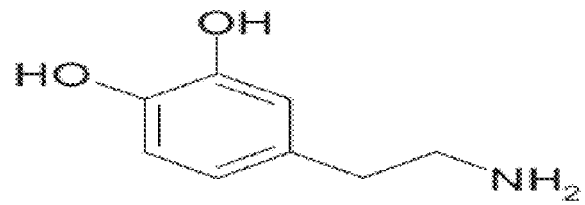
FIG. 1 shows the molecular structure and the associated physiochemical properties for the catecholamines (dopamine, noradrenaline, and adrenaline).
Figure 1:
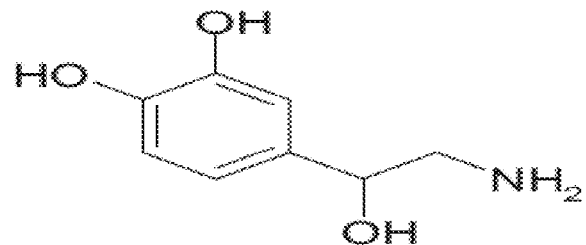
Figure 1:
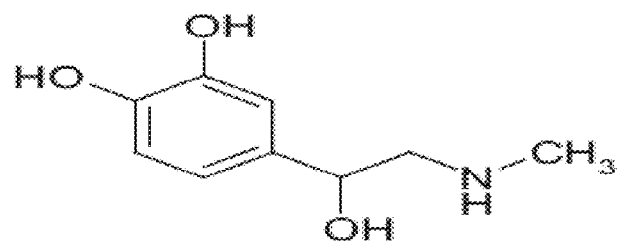

According to the present invention, the term "catecholamine" refers to naturally occurring catecholamines such as dopamine, epinephrine, and norepinephrine as well as synthetic catecholamines, i.e. catecholamines not found in nature, such as benserazide, carbidopa, dobutamine, dopexamine, isoprenaline and alpha-methyldopa, mixtures thereof and derivatives thereof.

Catecholamines determined by the method of the present invention may be contained in a sample derived from a natural source such as a biological sample from bodily fluids, serum, or plasma. Catecholamines determined by the method of the present invention may be contained in a sample derived from an artificial or synthetic source such as iv fluid.

Cis-diol or cis-diols refer to di-hydroxy alcohol(s) containing two hydroxyl groups connected to adjacent carbon atoms (1,2- or 1,3-) where both hydroxyl groups are on the same side of the molecules. These include glycols, such as ethylene glycol, and some sugars, such as glucose.

A biological sample refers to any sample from a biological source and is usually plasma or serum. Any fluid that can be isolated from the body of an individual is considered a biological sample. For example but not limited to, body fluid may include, blood, plasma, serum, bile, saliva, urine, tears, perspiration, and the like.

The biological samples are obtained by methods known in the art such as venous puncture. Preferably, the biological samples is a blood, serum, plasma, or other source taken from a health animal or human or from an animal or human afflicted with a disease or other condition.

Chromatography refers to a process in which a chemical mixture carried by a liquid or gas is separated into components as a result of differential distribution of the chemical entities between a stationary liquid or solid phase and a flowing liquid or gas.

Liquid chromatography (LC) means a process of selectively retarding one or more components of a fluid solution as the fluid uniformly percolates through a column of a finely divided substance, or through capillary passageways. The retardation results from the distribution of the components of the mixture between one or more stationary phases and the bulk fluid, (i.e. mobile phase), relative to the stationary phase and the related chemical processes, thereof. Liquid chromatography includes reverse phase liquid chromatography (RPLC), normal phase chromatography and a host of other chemistries to facilitate a separation process. Certain forms of liquid chromatography are carried out using HPLC.

High performance liquid chromatography (HPLC) refers to liquid chromatography in which the degree of separation is increased by forcing the mobile phase under pressure through a stationary phase, typically a densely packed column.

Mass spectrometry (MS) refers to an analytical technique to identify compounds by their mass to charge (m/z) ratio, MS technology generally includes four components: (1) sample introduction, e.g. HPLC; (2) ionizing the compounds to form charged compounds; (3) separation of the produced ions; and (4) detecting the charged species by monitoring mass to charge ratios. The compound may be ionized and then detected by any suitable means. See U.S. Pat. No. 6,204,500 "Mass Spectrometry From Surfaces"; U.S. Pat. No. 6,107,623 "Methods and Apparatus for Tandem Mass Spectrometry"; U.S. Pat. No. 6,268,144 "DNA diagnostics Based on Mass Spectrometry" U.S. Pat. No. 6,124,137 "Surface-Enhanced Photolabile Attachment and Release for Desorption and Detection of Analytes", Wright et al "Prostate Cancer and Prostate Diseases 2:264-276 (1999); and Merchan and Weinberger, Electrophoresis 21:1164-1167 (2000), all incorporated by reference.

Ionization refers to the process of generating an analyte ion having a net electrical charge equal to one or more electron units. Negative ions are those having a net negative charge of one or more electron units, while positive ions are those having a net positive charge of one or more electron units.

Operating in negative ion mode refers to those mass spectrometry methods where negative ions are detected. Similarly, operating in positive ion mode refers to those mass spectrometry methods where positive ions are detected.

A "fraction" obtained from a biological sample is through procedures known in the art to purify, fractionate, separate, etc. that portion of the biological sample with methods such as chromatography, ultrafiltration, precipitation, techniques, etc.

Terms such as "analyzing catecholamines" or "analyzing at least one catecholamine" relate to methods of measuring, collecting and analyzing data about catecholamines such as their relative or absolute concentration, their presence or absence etc. and include, in particular, the relative or absolute quantification of catecholamines.

The term "analyzing at least one catecholamine" according to the invention refers to an analysis of all or only a fraction of the catecholamines contained in a sample.

Terms such as "analyzing catecholamines" or "analyzing at least one catecholamine" according to the invention also includes situations wherein no catecholamines are detected or the amount of the catecholamines is below the detection limit.

According to the invention, a "reference sample" is used to correlate and compare the results obtained from a test sample. The composition of a "reference sample" is usually similar to a test sample but differs from the test sample in certain variables. For example, the test sample may be derived from an individual suspected of being afflicted with a disease while the reference sample is obtained from a healthy individual and/or an individual known to be afflicted with the disease.

According to the invention, the term "derivative" in connection with a particular compound or groups of compounds refers to a modified form of the compound(s). In one embodiment, a derivative of a compound retains the function or activity of the parent compound. In another embodiment the derivatization of a compound creates a property which was not present in a parent compound or modifies, preferably enhances a property of a parent compound such as the stability of catecholamines. Preferably, a derivative of a compound comprises one or more substituents at one or more positions of the parent compound. Derivatives of a compound also includes substances were in the compound is only a minor constituent of the substance. For example, an RNA molecule may be considered as a derivative of a ribonucleotide. Particular examples of catecholamine derivatives or modified catecholamines are catecholamines modified by alkylation, preferably O-alkylation, more preferably O-methylation, and/or modified by acylation.

Description of the Embodiments

The present invention provides methods for quantitating the presence or amounts of dopamine, norepinephrine, and/or epinephrine in a plasma sample by tandem mass spectrometry that include: (a) spiking a heparin plasma sample with an internal standard; (b) extracting with a two-step liquid-liquid extraction specific for compounds containing cis-diol groups; (d) derivatizing the cis-diol containing compounds with benzoyl chloride, and (e) identifying and quantitating by 2D-LC-MS/MS.

In one embodiment, methods are provided for a quantitative measurement in a serum or plasma sample, by mass spectrometry, the amount of dopamine, norepinephrine, and/or epinephrine, that include: (a) extracting dopamine, norepinephrine, and/or epinephrine in the test sample by sample preparation processes and liquid chromatography; (b) ionizing dopamine, norepinephrine, and/or epinephrine; and (c) detecting the amount of dopamine, norepinephrine, and/or epinephrine via ions(s) produced by mass spectrometry and relating the amount of dopamine, norepinephrine, and/or epinephrine ion(s) to the amount of dopamine, norepinephrine, and/or epinephrine in the test sample. Results are reported in "pg/ml" for all three catecholamines.

In a preferred embodiment, methods are provided for determining the amount of dopamine, norepinephrine, and/or epinephrine in a plasma sample by tandem mass spectrometry that include: (a) combining an internal standard with dopamine, norepinephrine, and/or epinephrine; (b) extracting dopamine, norepinephrine, and/or epinephrine without drying to directly derivatize with benzoyl chloride under room temperature; and (c) using HPLC separation with electrospray LC-MS/MS identification and quantitation.

In certain embodiments of the methods disclosed herein, mass spectrometry is performed in positive ion mode. Alternatively, mass spectrometry is performed in negative ion mode. Other embodiments measure dopamine, norepinephrine, and/or epinephrine using both positive and negative ion mode.

In a preferred embodiment, separately detectable internal standards are added to the sample, the amount of which is also determined in the sample. The internal standards used include stable isotope labeled analogs of dopamine, norepinephrine, and/or epinephrine, thus constituting isotope dilution mass spectrometry. In these embodiments, all or a portion of both the endogenous dopamine, norepinephrine, and/or epinephrine and the internal standard present in the sample are ionized to produce a plurality of ions detectable in a mass spectrometer, and one or more ions produced from each are detected by mass spectrometry. Internal standards are dopamine-$d_4$, (+/−)-norepinephrine-$d_6$ and/or epinephrine-$d_6$.

In one embodiment, the methods involve the combination of liquid chromatography with mass spectrometry. In a preferred embodiment, the liquid chromatography is HPLC. A preferred embodiment utilized HPLC alone or in combination with one or more purification methods such as extracting dopamine, norepinephrine, and/or epinephrine from a fluid sample by solid-phase extraction. In another embodiment, the extraction from the fluid sample is by a two-step liquid-liquid extraction specific for compounds containing catechol groups such as, but not limited to, phenylboronic acid and tetraoctylammonium bromide.

In another embodiment, the extract is derivatized with benzoyl chloride. Benzoyl chloride reacts with primary and secondary amines, phenols, and ribose-hydroxyl groups under mild conditions with high yield, allowing multiple functional groups in one molecule to be derivatized. The derivatization conditions can be optimized and tailored to maximize the yield for a targeted analyte while minimizing the yield of other potentially interfering matrix components. The derivatives formed with benzoyl chloride are more hydrophobic so that they can be retained and separated by reverse phase chromatography. Derivatization with benzoyl chloride provides a convenient way to improve the sensitivity and quantitation by LC-MS/MS, especially when a commonly produced ion m/z 105 originated from benzoyl moiety is used in multiple reaction monitoring. Besides benzoyl chloride, other acyl halides with a benzoyl ring or benzoyl moiety, or other functional groups that do not carry a charge in the parent ion and do carry a charge in production after the parent ion is fragmented in MS/MS can be substituted for benzoyl chloride.

In still another embodiment, the preferred HPLC instrument is 2D-LC that provides the advantages of high separation power and specificity. Accordingly, the assay is sensitive, robust and reproducible.

In another embodiment, the mass spectrometry is tandem mass spectrometry (MS/MS).

In general, methods described use mass spectrometry for detecting and quantifying dopamine, norepinephrine, and/or epinephrine in a test sample. Certain aspects of the invention involve isolating the compounds of interest, ionizing the compounds of interest, detecting the ion(s) by mass spectrometry, and relating the presence or amount of the ion(s) and the presence or amount of catecholamine(s) in the sample.

Certain embodiments are particularly well suited for application in large clinical laboratories. Methods of detecting and quantifying dopamine, norepinephrine, and/or epinephrine are provided that have enhanced specificity and/or are accomplished in less time and with less sample preparation than required in prior assays.

As a general assay, other embodiments are particularly well suited for detecting the presence, monitoring the level, or determining the concentration of compounds containing cis-diol groups, such as glycols, nucleic acid components, sugars, polyols, catechols and glycosylated proteins.

Test Samples

Suitable test samples include any test sample that may be obtained from any biological source, such as an animal, a cell culture, an organ culture, etc. In certain embodiments, samples are obtained from a mammalian animal, such as a dog, cat, horse, etc. Exemplary mammalian animals are primates, most preferably humans. Exemplary samples include blood, plasma, serum, hair, muscle, urine, saliva, tear, cerebrospinal fluid, or other tissue sample, however plasma is the preferred test sample. Such samples may be obtained, for example, from a patient; that is, a living person presenting oneself in a clinical setting for diagnosis, prognosis, or treatment of a disease or condition. The test sample may be obtained from a patient, for example, blood serum. Samples may also be harvested from deceased individuals. Because catecholamines are extremely labile, it is critical that the sample be collected and stored in a polypropylene collection chamber.

Sample Preparation for Mass Spectrometry

Figure 2:
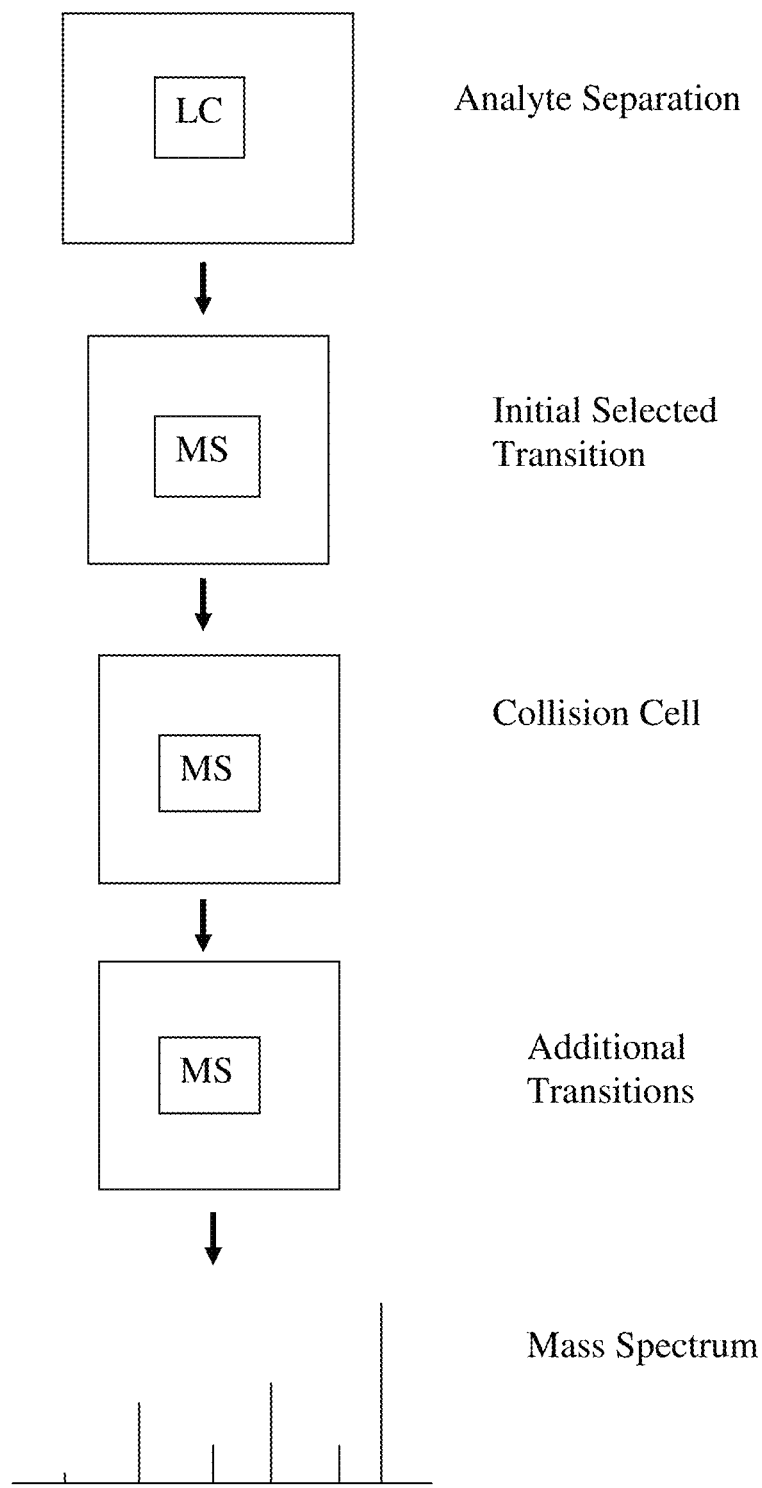
FIG. 2 is a schematic of the steps in LC-MS/MS analysis of catecholamines such as dopamine, epinephrine, and norepinephrine.

FIG. 2 shows a schematic of the analysis of catecholamines such as dopamine, epinephrine, and norepinephrine. Methods used prior to mass spectrometry can enrich catecholamines relative to other components in the sample, or to increase the concentration of catecholamines in the sample. While such methods include, for example, filtration centrifugation, thin layer chromatography, electrophoresis including capillary electrophoresis, affinity separations including immunoaffinity separations and extraction methods, including solid phase extraction by cation exchange or any combination of the above or the like, the preferred embodiment of the present invention incorporates an enrichment and extraction process involving a two-step liquid-liquid extraction specific for compounds containing catechol groups and using phenylboronic acid and tetraoctylammonium bromide.

Because of the cis-diol specific activity of these compounds, a two-step liquid-liquid enrichment and extraction using the methods of the present invention are considered. Any agent capable of selectively binding cis-diol to form a stable cyclic borate via a complex formation through covalent bonding is considered as an extraction agent in the present invention. Phenylboronic acid is known to selectively bind cis-diol and is considered also as an extracting agent. Without drying the extract is directly derivatized with benzoyl chloride under room temperature before injection without further cleanup.

Generally, any analyte or compound containing at least one cis-diol structure is considered in the present invention. This includes compounds such as, but not limited to, 1,2-dihydroxyalkanes, polyphenols, 2-hydroxyacids, ascorbic acid, carbonhydrates, derivatives thereof and mixtures thereof. The 1,2-dihydroxyalkane may be ethanediol, 1,2-propanediol, or an alkanediol comprising vicinal hydroxyl groups. The polyphenol may be a catechol, anthocyane, gallic acid, or tannin. The 2-hydroxyacid may be lactic acid, tartaric acid, or citric acid. The carbohydrate may be a monosaccharide, a disaccharide, an oligosaccharide or a polysaccharide.

Samples may then be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography.

Liquid Chromatography

Generally, chromatography may be performed prior to mass spectrometry; the chromatography may be liquid chromatography, such as high performance liquid chromatography.

Liquid chromatography including high-performance liquid chromatography rely on relatively slow, laminar flow technology. Traditional HPLC analysis relies on column packing in which laminar flow of the sample and mobile phase through the column is the basis for separation of the analyte of interest from the sample. The skilled artisan will understand that separation in such columns is a diffusional process. HPLC has been successfully applied to the separation of some compounds in biological samples. But a significant amount of sample preparation is required prior to the separation and subsequent analysis with a mass spectrometer, making this technique labor intensive. In addition, most HPLC systems do not utilize the mass spectrometer to its fullest potential, allowing only one HPLC system to be connected to a single MS instrument, resulting in lengthy time requirements for performing a large number a of assays.

The preferred HPLC would include a system that is able to utilize two sets of binary pumps for 2D-LC-MS/MS such as a Shimadzu HPLC system.

In certain embodiments, an analyte may be purified by applying a sample to a column under conditions where the analyte of interest is reversibly retained by the column packing material while one or more other materials are not retained. In these embodiments, a first mobile phase condition can be employed where the analyte of interest is retained by the column and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the samples.

Detection and Quantification by Mass Spectrometry

The present invention discloses mass spectrometric methods for detecting the presence or amount of catecholamines such as dopamine, epinephrine, and norepinephrine in a sample. In certain aspects, the method involves a two-step liquid-liquid extraction of catecholamines, ionizing the compounds, detecting the ion(s) by mass spectrometry, and relating the presence or amount of the ion(s) to the presence or amount of catecholamines in the sample.

Mass spectrometry may be performed using a mass spectrometer which includes an ion source for ionizing the fractionated sample and creating charged molecules for further analysis. For example, ionization of the sample may be performed by electrospray ionization, atmospheric pressure chemical ionization, atmospheric pressure photoionization, photoionization, electron ionization, fast atom bombardment/liquid secondary ionization, matrix assisted laser desorption ionization, field ionization, field desorption, thermospray/plasmaspray ionization, and particle beam ionization. The skilled artisan will understand that the choice of ionization method can be determined based on the analyte to be measure, type of sample, the type of detector, the choice of positive versus negative mode, etc.

After the sample has been ionized, the positively charged or negatively charged ions thereby created may be analyzed to determine a mass-to-charge ratio (i.e. m/z). Suitable analyzers for determining mass-to-charge ratios include, but are not limited to, quadrupole analyzers, ion trap analyzers, and time-of-flight analyzers. The ions may be detected using several detection modes. For example, selected ions may be detected (e.g. using a selective ion monitoring mode (SIM), or alternatively, ions may be detected using a scanning mode e.g. multiple reaction monitoring (MRM) or selected reaction monitoring (SRM). The mass-to-charge ratio is determined using a quadrupole, or other, analyzer. For example, in a quadrupole or quadrupole ion trap instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a mass filter and as a mass detector for the ions injected into the instrument.

One may enhance the resolution of the MS technique by employing tandem mass spectrometry or MS/MS. In this technique, a precursor ion (also called a parent ion) generated from a molecule of interest can be filtered in an MS instrument and the precursor ion is subsequently fragmented to yield one or more fragments ions (also called daughter ions or product ions) that are then analyzed in a second MS procedure. By careful selection of precursor ions, only ions produced by certain analytes are passed to the fragmentation chamber, where collision with atoms of an inert gas produce the daughter ions. Because both the precursor and fragment ions are produced in a reproducible fashion under a given set of ionization/fragmentation conditions, the MS/MS technique can provide an extremely powerful analytical tool. For example, the use of tandem mass spectrometry (MS/MS) can be used to eliminate interfering substances, and can be particularly useful in complex samples, such as biological samples.

The mass spectrometer typically provides the user with an ion scan; that is, the relative abundance of each ion with a particular m/z over a given range (e.g. 100 to 200 amu). The results of an analyte assay, that is, a mass spectrum, can be related to the amount of the analyte in the original sample by numerous methods known in the art. For example, standards (a.k.a. calibrators) can be run with the samples, and a standard curve constructed based on ions generated from those standards. Using such a standard curve, the relative abundance of a given ion can be converted into an absolute amount of the molecule present in the sample. In certain embodiments, an internal standard is used as a reference compound to facilitate generation of a standard curve for calculating the quantity of catecholamines. Methods of generating and using such standard curves are well known in the art and one of ordinary skill is capable of selecting an appropriate internal standard. For example, dopamine-$d_4$ as an internal standard for dopamine; (+/−)-norepinephrine-$d_6$ as an internal standard for norepinephrine; and epinephrine-$d_6$ as an internal standard for epinephrine can be used. Numerous other methods for relating the presence or amount of an ion to the presence or amount of the original molecule will be well known to those of ordinary skill in the art.

In certain embodiments such as MS/MS where precursor ions are isolated for further fragmentation, collision activation dissociation (CAD) is often used to generate the fragment ions for further detection. In CAD, precursor ions gain energy through collisions with an inert gas, and subsequently fragment by processes, including but not limited to, unimolecular decomposition. Sufficient energy must be deposited in the precursor ion so that certain bonds within the ion can be broken due to, but not limited to, increased vibrational energy.

In certain embodiments, catecholamines are detected and quantified using LC-MS/MS as follows (see FIG. 2). The samples are subjected to liquid chromatography. The flow of liquid solvent from the chromatographic column enters the heated nebulizer interface of a LC-MS/MS analyzer and the solvent/analyte mixture is converted to vapor in the heated tubing of the interface. The analytes contained in the nebulized solvent are ionized through a series of processes involving drying gases, charge application, etc. The pre-selected ions, i.e. precursor ions, pass through the orifice of the instrument and enter the first quadrupole. Quadrupoles 1 and 3 (Q1 and Q3) are mass filters, allowing selection of ions (i.e. precursor and fragment ions) based on the mass to charge ratio (M/Z). Quadrupole 2 (Q2) is the collision cell where precursor ions are fragmented. The first quadrupole of the mass spectrometer (Q1) selects molecules with the mass to charge ratios of the specific niacin and active metabolite moieties to be analyzed. Precursor ions with the correct m/z ratios of the precursor ions of the specific niacin or active metabolite moiety are allowed to pass into the collision chamber (Q2) while unwanted ions with any other m/z collide with the sides of the quadrupole and are eliminated or pumped away. Precursor ions entering Q2 collide with neutral Argon gass molecules and fragment. This process is called Collision Activated Dissociation (CAD). The fragment ions generated are passed into quadrupole 3 (Q3) where the fragment ions of the desired niacin or active metabolite moiety are selected while other ions are eliminated.

The methods of the invention may involve MS/MS performed in either positive or negative ion mode. Using standard methods well known in the art, one of ordinary skill is capable of identifying one or more fragment ions of a particular precursor ion of an niacin or active metabolite that can be used for selection in quadrupole 3 (Q3).

In one embodiment, ions collide with the detector and produce a pulse of electrons that are converted to a digital signal. Other detector physics/engineering can be used, e.g., time of flight. The acquired data is relayed to a computer which plots counts of the ions collected versus time. The resulting mass spectra are similar by analogy to chromatograms generated in traditional HPLC methods. The areas under the peaks corresponding to particular ions, or the amplitude of such peaks are measured and the area or amplitude is correlated to the amount of the analyte (catecholamine moiety) of interest. In certain embodiments, the area under the curves or amplitude of the peaks, for fragment ion(s) and precursor ions are measured to determine the amount of catecholamine moiety. As described above, the relative abundance of a given ion can be converted into an absolute amount of the original analyte, i.e. catecholamine moiety, using calibration standard curves based on peaks of one or more ions of the catecholamine moiety of interest and an internal standard.

In certain aspects of the invention, the quantity of various ions is determined by measuring the area under the curve or the amplitude of the peak and a ratio of the quantities of the ions is calculated and monitored (i.e. daughter ion ratio monitoring). In certain embodiments of the method, the ratio(s) of the quantity of a precursor ion and the quantity of one or more fragment ions of catecholamine can be calculated and compared to the ratio(s) of a standard of the catecholamine moiety similarly measured. In embodiments where more than one fragment ion of an niacin or active metabolite is monitored, the ratio(s) for different fragment ions may be determined instead of, or in addition to, the ratio of the fragment ion(s) compared to the precursor ion. In embodiments where such ratios are monitored, if there is a substantial difference in an ion ratio in the sample as compared to the standard, it is likely that a molecule in the sample is interfering with the results or some other analytical phenomenon is in practice. To the contrary, if the ion ratios in the sample and the molecular standard are similar, then there is increased confidence that there is no interference. Accordingly, monitoring such ratios in the samples and comparing the ratios to those of authentic standards may be used to increase the accuracy of the method.

In certain embodiments of the invention, the presence or absence of an amount of two or more catecholamine moieties in a sample might be detected in a single assay using the above described MS/MS methods.

Figure 3:
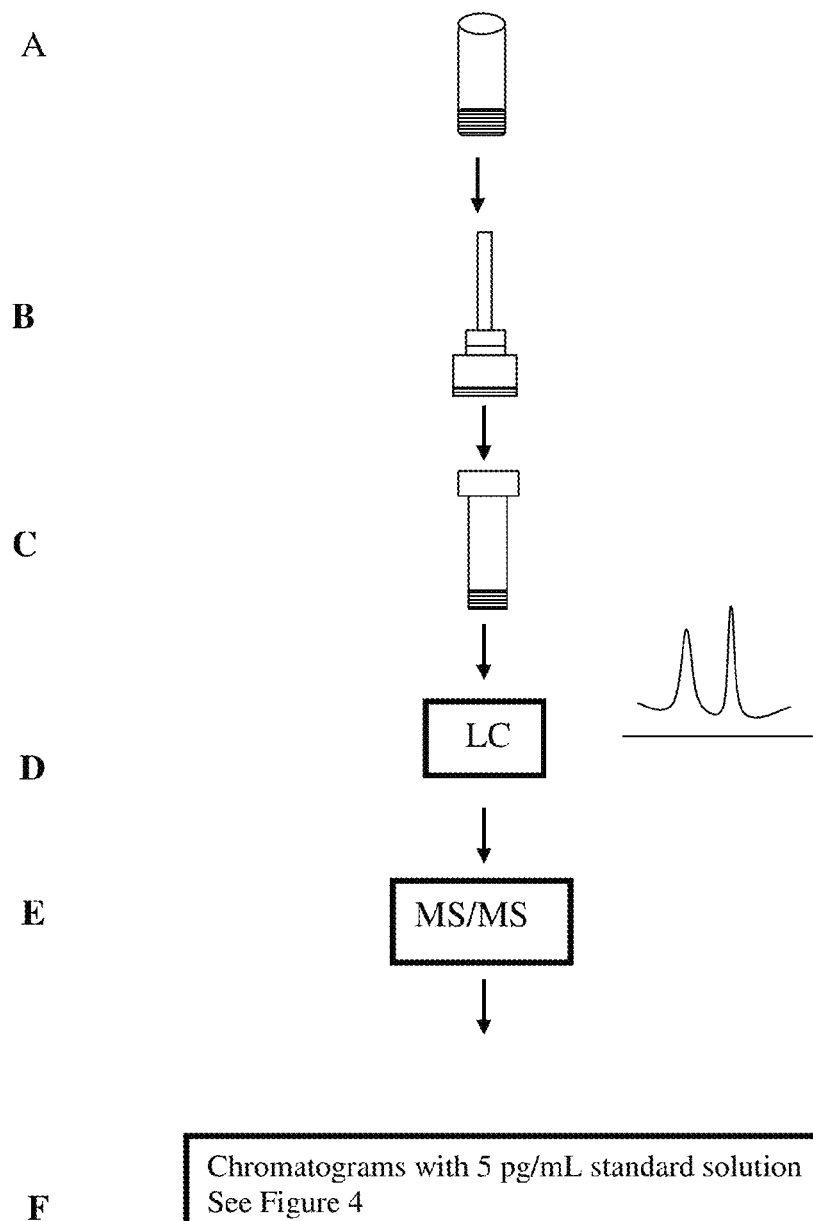
FIG. 3 is a schematic of the steps in the analysis of catecholamines from a fluid sample.

A representation of the steps in catecholamine processing and analysis is shown schematically in FIG. 3. "A" is a plastic (e.g. polypropylene) collection chamber used to collect samples for analytes containing the catechol moieties. Using standard clinical laboratory techniques, the serum or plasma is prepared for extraction. "B" and "C" represent the two-step liquid-liquid extraction specific for compounds containing catechol groups using phenylboronic acid and tetraoctylammonium bromide. The extract is directly derivatized with benzoyl chloride under room temperature before injected into the LC as shown in "D". In "E", ions are formed within the first MS, a pre-selected transition (Q1) is forwarded to the collision cell (Q2) whereby additional preselected ion transitions are sorted by Q3. In "F", the transition tracing are produced and the amount of each metabolite quantitated.

Figure 4:
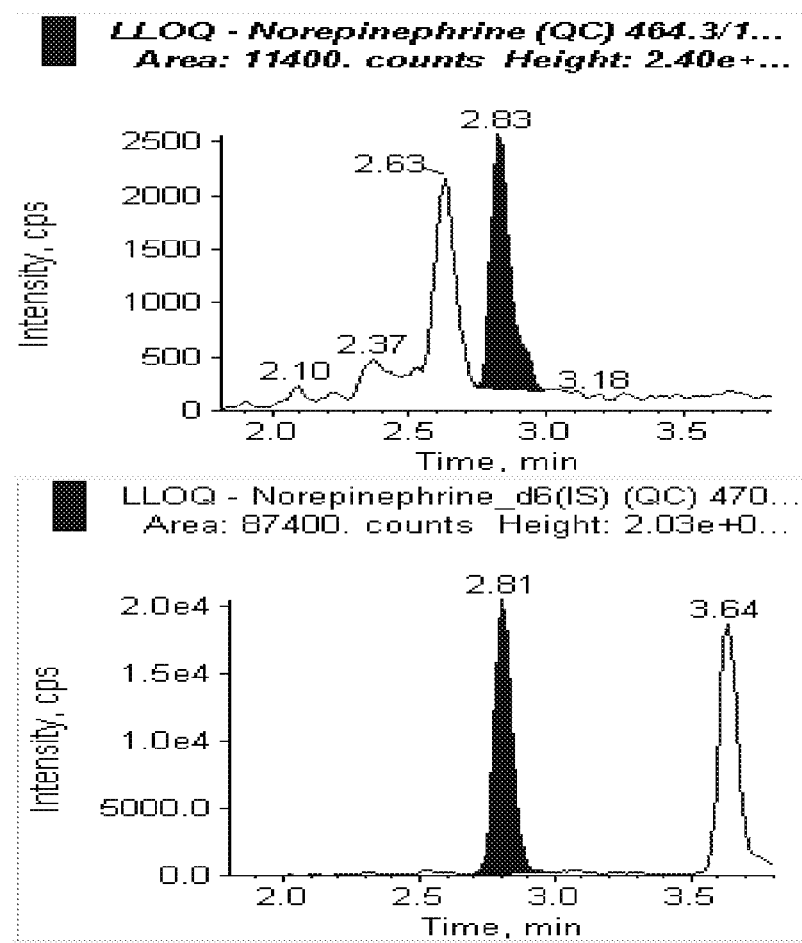
FIG. 4 chromatograms using 5 pg/mL standard solution for dopamine, epinephrine, and norepinephrine from a fluid sample. Panel A is norepinephrine, Panel B is epinephrine, and Panel C is dopamine.
Figure 4:
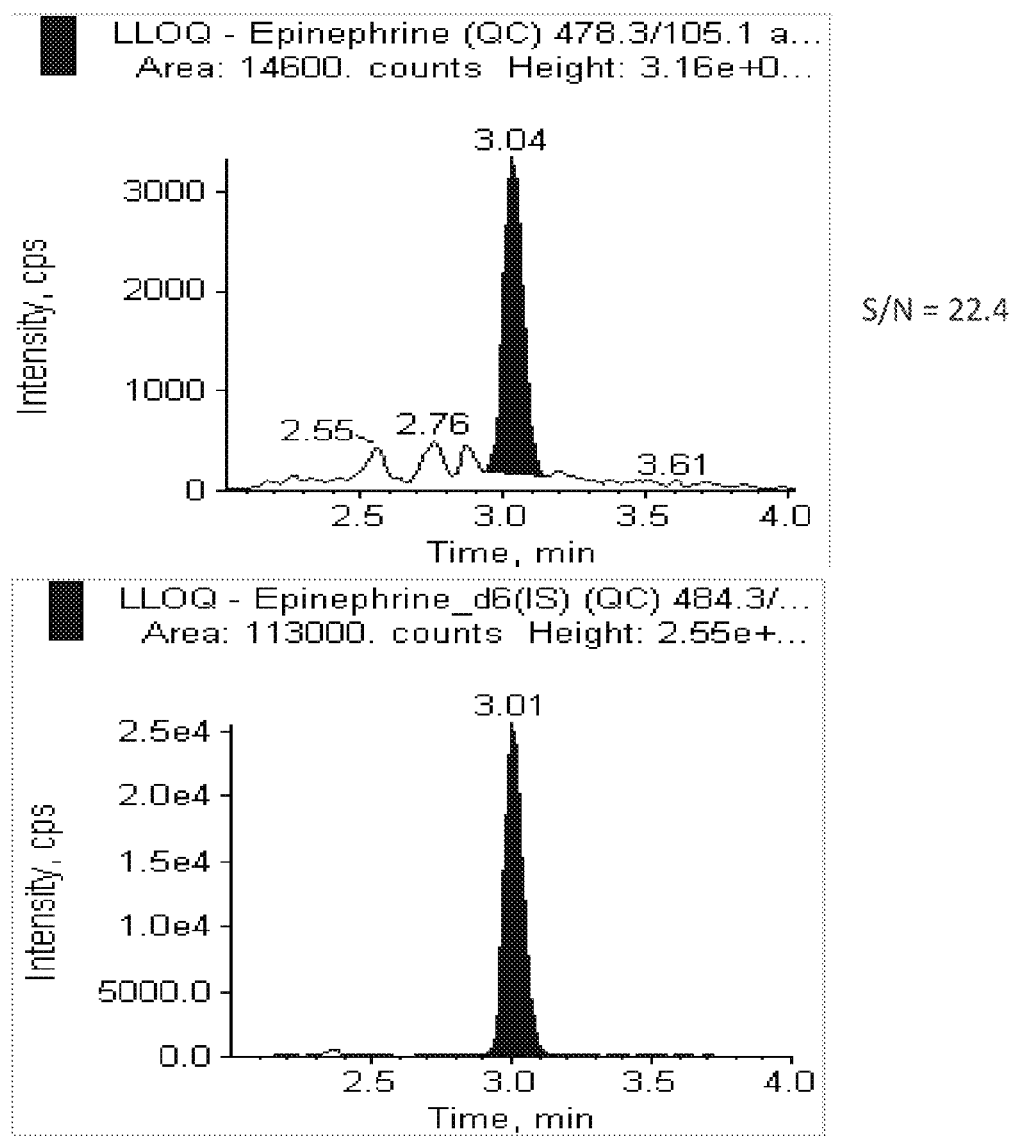
Figure 4:
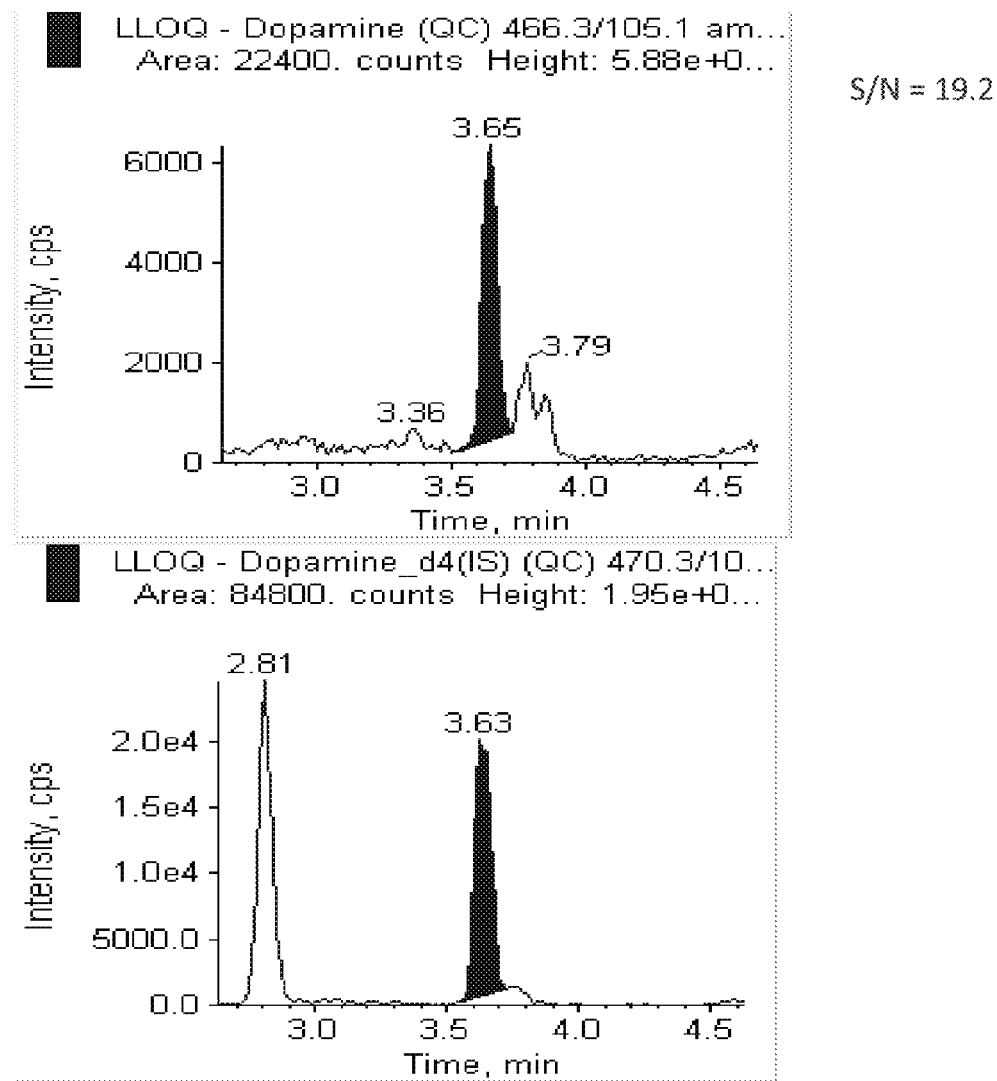

FIG. 4 shows typical chromatograms for catecholamine moieties. Norepinephrine is shown in Panel A; epinephrine is shown in Panel B, and dopamine is shown in Panel C.

Comparison of 2D-LC-MS/MS with HPLC

One aspect of the invention is related to a method for assessing the amount of dopamine, epinephrine and norepinephrine in a sample comprising the steps of: (a) taking an aliquot of sample; (b) mixing with an internal standard; (c) extracting with a two-step liquid-liquid extraction; (d) derivatizing with benzoyl chloride; (e) injecting derivatized sample into an HPLC; (f) analyzing by mass spectrometry, thereby generating a plurality of ions; and (g) detecting and quantifying one or more ions.

Because catecholamines in plasma are extremely labile, stability is strongly dependent upon the special attention used during specimen collection, processing, storage, and transportation.

For the sample preparation, human plasma is promptly centrifuged and the plasma separated into a plastic screw capped vial. An aliquot of 200 µL of heparin plasma is mixed with 20 µL of working internal standard (0.5 ng/mL of each, dopamine-$d_4$, epinephrine-$d_6$, and norepinephrine-$d_6$), and extracted with a two-step liquid-liquid extraction specific for compounds containing catechol groups, using phenylboronic acid and tetraoctylammonium bromide. The extract without drying is directly derivatized with benzoyl chloride under room temperature before injection without further cleanup.

An API-5000 triple-quadrupole mass spectrometer (AB Sciex) is coupled to a Shimadzu HPLC system of two sets of binary pumps for 2D-LC-MS/MS. The $1^{st}$ D-LC uses Gemini C18 guard columns (4×2.0 mm) for online extraction and cleanup with 5 mM $NH_4HCO_3$ in water and acetonitrile as mobile phase while the $2^{nd}$ D-LC uses a Gemini C6 Phenyl column (50×2.0 mm) for analytical separation using the same mobile phase as $1^{St}$ D. A six-port switching valve is switched at 0.5 min and 1.7 min to transfer compounds of interest from $1^{st}$ D to $2^{nd}$ D in heart-cutting fashion without back flash. The API 5000 is operated in positive electrospray and multiple reaction monitoring (MRM) mode with two MRMs monitored for each analyte or internal standard.

Figure 5:
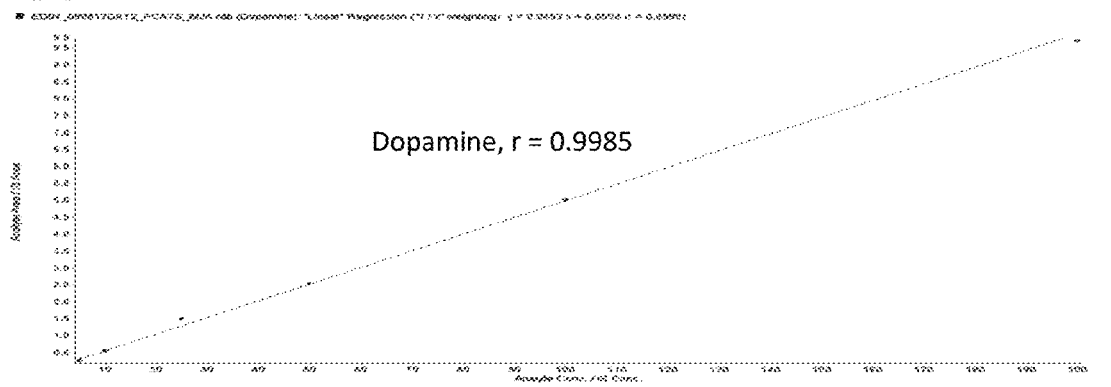
FIG. 5 shows standard curves generated for dopamine (Panel A) r=0.9985, norepinephrine (Panel B) r=0.9991, and epinephrine (Panel C) r=0.9993, FIG. 6 compares 2D-LC-MS/MS with high performance liquid chromatography (HPLC) using electrochemical detection (ECD) using simple linear regression for dopamine (Panel A), norepinephrine (Panel B), and epinephrine (Panel C).
Figure 5:
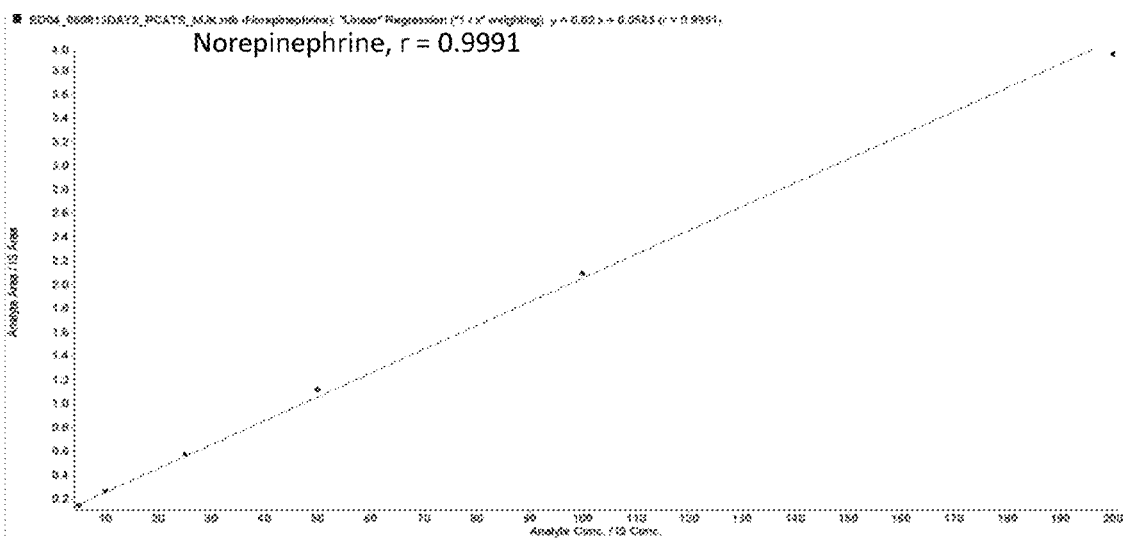
Figure 5:
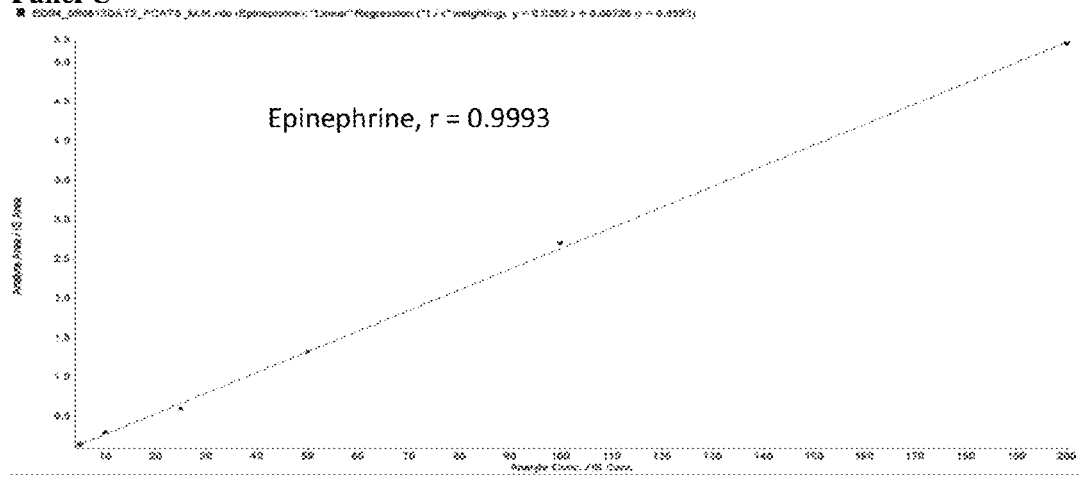

Calibration curves were constructed with chromatographic peak area ratios (analyte versus internal standard). FIG. 5 shows the standard curves generated for dopamine (Panel A) with r=0.9985, norepinephrine (Panel B) with r=0.9991, and epinephrine (Panel C) with r=0.9993. The lower limit of quantification was validated at 5 pg/mL for dopamine, norepinephrine, and epinephrine, having an accuracy of greater than 89.3% (CV<10.43%), while the upper limit of quantification was validated at 1000 pg/mL for dopamine, norepinephrine, and epinephrine, having an accuracy of greater than 91.7% (CV<6.72%). Within the run CV's for dopamine, norepinephrine, and epinephrine were less than 8.61% for three QCs and less than 8.89% for dopamine, norepinephrine, and epinephrine between runs. Extraction recovery was approximately 60% and no matrix effect was observed.

When compared with high performance liquid chromatography (HPLC) followed by electrochemical detection (ECD) and analyzed using Deming regression (EP Evaluator), the following values were obtained;

$$\text{dopamine } y=0.961(X_{HPLC\text{-}ECD})+19.859, r=0.9738, n=31 \qquad \text{A)}$$

$$\text{norepinephrine } y=1.023(X_{HPLC\text{-}ECD})+11.76, r=0.9967, n=32 \qquad \text{B)}$$

$$\text{epinephrine } y=1.036(X_{HPLC\text{-}ECD})+9.281, r=0.9957, n=36 \qquad \text{C)}$$

Figure 6:
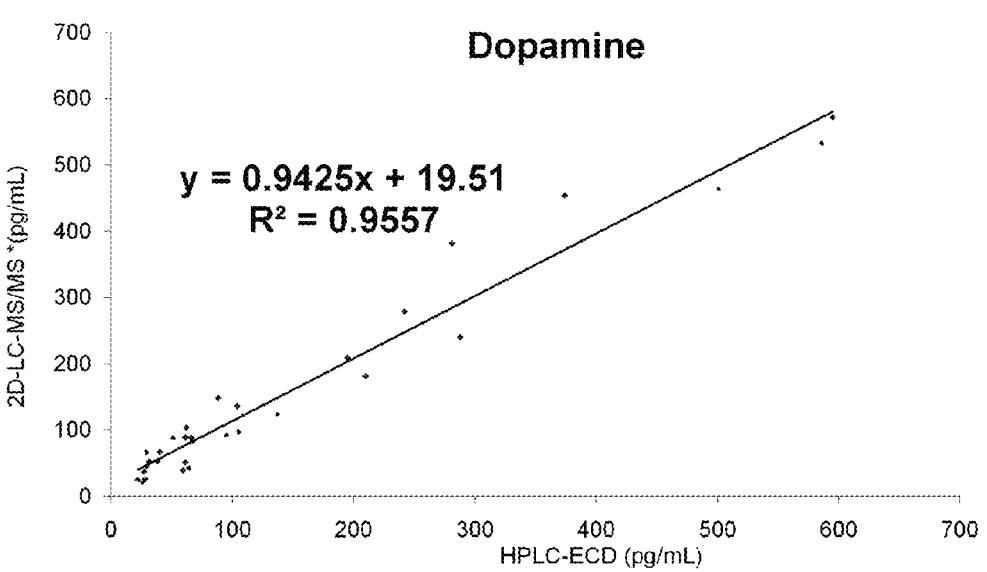
Figure 6:
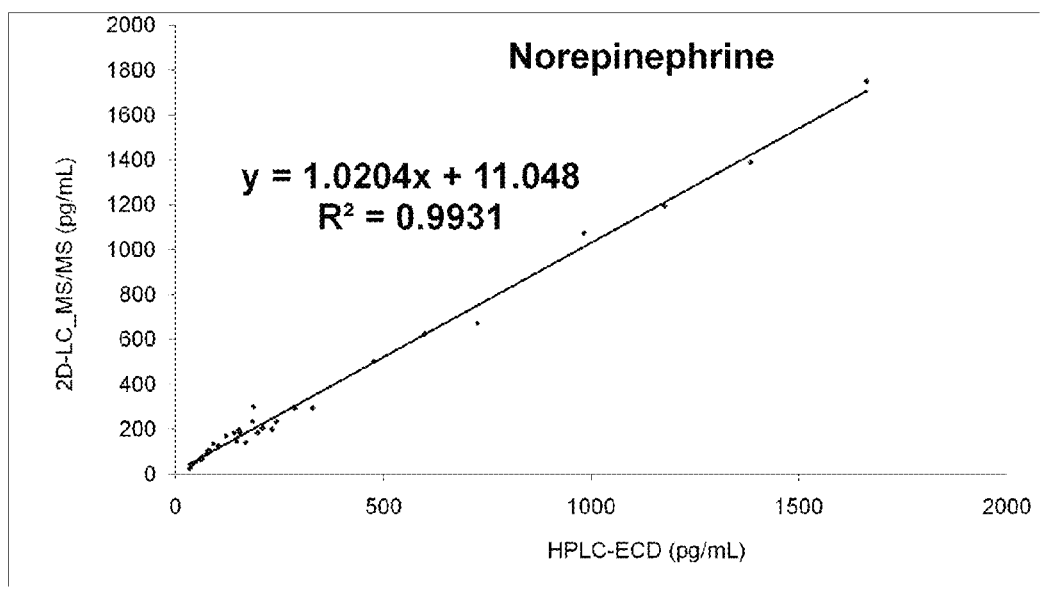
Figure 6:
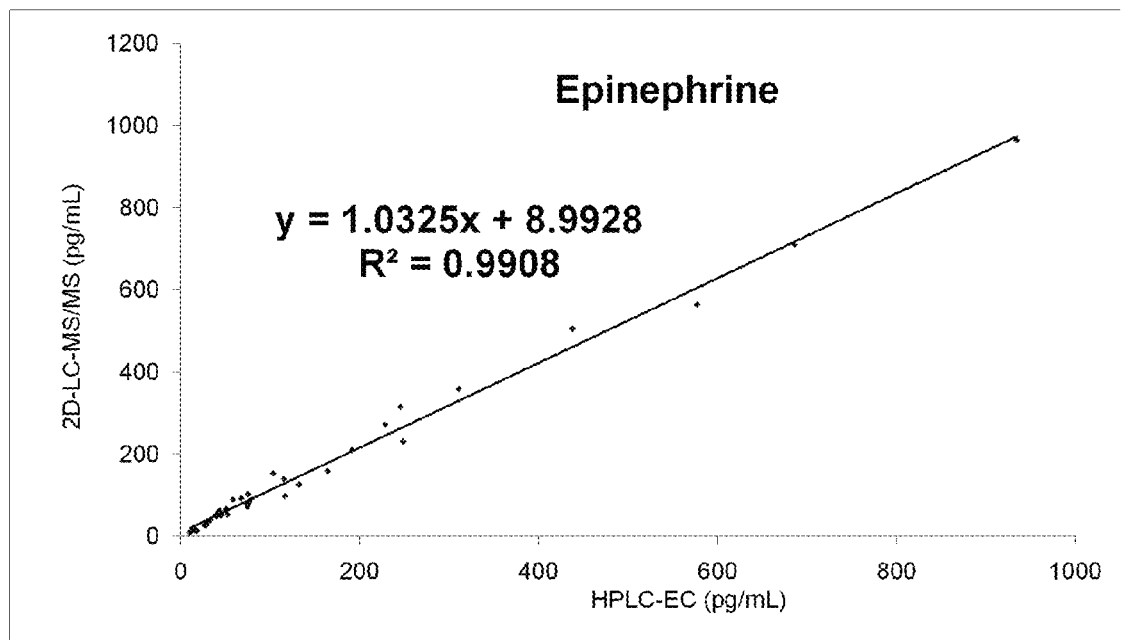

FIG. 6 shows the comparison between the method of the present invention using 2D-LC-MS/MS and high performance liquid chromatography (HPLC) using electrochemical detection (ECD) and analyzed by simple linear regression. Panel A is a best fit linear graph for a two-dimensional dataset dopamine with y=0.9425($X_{HPLC\text{-}ECD}$)+19.51, $R^2$=0.9957. Panel B is a best fit linear graph for norepinephrine with y=1.0204($X_{HPLC\text{-}ECD}$)+11.048, $R^2$=0.9931. Panel C is a best fit linear graph for epinephrine with y=10.0325($X_{HPLC\text{-}ECD}$)+0.9908, $R^2$=0.9908.

This example shows that the method of the present invention provides a sensitive and specific method to accurately quantify at least three catecholamines such as, but not limited to, dopamine, norepinephrine, and epinephrine in heparin plasma by 2D-LC-MS/MS. Using a 200 uL sample volume can be analyzed within a five minute run time and having 5 pg/mL as the lower limit of quantification (LLOQ).

Clinical Relevance

Prior to the present invention there has been large variability with respect to the sensitivity and specificity of serum/ plasma concentrations of catecholamines. Consequently, it has not been possible to establish a reference or standard procedure to confidently gauge clinical samples for reporting.

Therefore, an analysis that can simultaneously quantify catecholamines in serum/plasma would be useful in the diagnosis and treatment of diseases such as, but not limited to, hypertension and pheochromocytoma. The method of the present invention can be used to establish normal concentrations for all three catecholamines or each individual catecholamine moiety while also monitoring the levels of all three catecholamines during treatment or diagnosis of disease states.

The present invention also has applications in the rapid and efficient analysis of large numbers of samples in clinical or research setting. Because of the rapid sample preparation and direct injection of the extracted sample for 2D-LC-MS/MS, the method can be easily automated.

Selected Kits

The present invention also provides specimen collection kits for conveniently and effectively measuring the amount of catecholamines in a biological sample. In certain embodiments, the kit contains specific collection vials containing specific chemicals to stabilize and facilitate catecholamine analyses.

A kit of invention may include instructions in any form that are provided in connection with the methods of the invention in such a manner that one of ordinary skill in the art would recognize said instructions and realize they are associated with the methods of the invention.

The invention requires the collection and storage of samples in pre-defined tubes and temperatures. Such directions are associated with the proper testing of all catecholamine samples.

Applicants reserve the right to physically incorporate into this application any and all materials and information from any such articles, patents, patent applications, or other physical and electronic documents.

Methods illustrated herein may suitably be practiced in the absence of any element or elements, limitation or limitation, not specifically disclosed herein. The terms and expressions used herein have been used as terms of description and not of limitation, and there is no intention in the use of such terms of excluding any equivalents of the features shown and described or portions thereof. It is recognized that various modification are possible within the scope of the invention claimed. Thus, it should be understood that although the present invention has been specifically disclosed by preferred embodiments and other features, modification and variation of the invention embodied therein herein disclosed may be used by those skilled in the art, and that such modification and variations are considered to be within the scope of this invention.

The invention has been described broadly and generically herein. Each of the narrower species and sub-generic grouping falling within the generic disclosure also form part of the methods. This includes the generic description of the methods with a proviso or negative limitation that removing any subject matter from the genus, regardless of whether or not the excised material is specifically recited herein.

The invention claimed is:

1. A method for determining the amount of one or more analytes having at least one cis-diol structure in a sample, the method comprising:
   a. obtaining an aliquot of a sample suspected of containing at least one analyte having at least one cis-diol structure;
   b. mixing the aliquot with an internal standard;
   c. extracting the analyte from the aliquot by adding a compound that binds cis-diol to form a stable cyclic borate complex wherein the extraction is completed without drying;
   d. derivatizing an extract with a compound having a benzoyl moiety under room temperature;
   e. separating a derivatized extract from step d by high pressure liquid chromatography (HPLC);
   f. subjecting a separated and derivatized extract from step e to electrospray ionization (ESI) under conditions suitable to produce one or more ions detectable by mass spectrometry; and
   g. determining an amount of one or more ions by mass spectrometry, whereby the amount of one or more ions reflects an amount of one or more analytes in the sample.

2. The method of claim 1, wherein one or more analytes are selected from a group of cis-diol containing compounds consisting of glycols, polyols, nucleic acids, glycosylated peptide/proteins, 1,2-dihydroxyalkanes, polyphenols, 2-hydroxyacids, catechols, ascorbic acid, carbohydrates, derivatives thereof and mixtures thereof.

3. The method of claim 1, wherein the compound that binds cis-diol to form a stable cyclic borate is a compound containing a phenylboronic acid moiety.

4. The method of claim 1, wherein the compound that binds cis-diol to form a stable cyclic borate is phenylboronic acid.

5. The method of claim 1, wherein the compound having a benzoyl moiety is an acyl halide.

6. The method of claim 1, wherein the compound having a benzoyl moiety is benzoyl chloride.

7. The method of claim 1, wherein one or more analytes are selected from the group consisting of epinephrine, norepinephrine, dopamine and combinations thereof.

8. The method of claim 1, wherein the amounts of two or more of the analytes selected from the group consisting of epinephrine, norepinephrine, and dopamine are determined from the same derivatized extract.

9. The method of claim 1, wherein the analytes are purified by high performance liquid chromatography (HPLC) prior to ionization.

10. The method of claim 1, wherein mass spectrometry is tandem mass spectrometry.

11. The method of claim 1, wherein separating and mass spectrometry is 2D-LC-MS/MS.

12. A method for determining the amount of catecholamines in a sample, the method comprising:
   a. obtaining an aliquot of a sample suspected of containing at least one analyte having at least one catecholamine;
   b. mixing the aliquot with an internal standard;
   c. extracting the analyte from the sample by adding a compound that binds cis-diol to form a stable cyclic borate wherein the extraction is completed without drying;
   d. derivatizing an extract with a compound having a benzoyl moiety under room temperature;
   e. separating a derivatized extract from step d by high pressure liquid chromatography (HPLC);
   f. subjecting a separated and derivatized extract from step e to electrospray ionization (ESI) under conditions suitable to produce one or more ions detectable by mass spectrometry; and
   g. determining the amount of the one or more ions by mass spectrometry, whereby the amount of the one or more ions reflects the amount of one or more analytes in the sample.

13. The method of claim 12, wherein one or more analytes are selected from the group consisting of epinephrine, norepinephrine, dopamine and combinations thereof.

14. The method of claim 12, wherein the compound that binds cis-diol to form a stable cyclic borate is a compound containing a phenylboronic acid moiety.

15. The method of claim 12, wherein the compound that binds cis-diol to form a stable cyclic borate is phenylboronic acid.

16. The method of claim 12, wherein the compound having a benzoyl moiety is benzoyl chloride.

17. The method of claim 12, wherein the amounts of two or more of the analytes selected from the group consisting of epinephrine, norepinephrine, and dopamine are determined from the same derivatized extract.

18. The method of claim 12, wherein the analytes are purified by high performance liquid chromatography (HPLC) prior to ionization.

19. The method of claim 12, wherein mass spectrometry is tandem mass spectrometry.

20. The method of claim 12, wherein separating and mass spectrometry is 2D-LC-MS/MS.

\* \* \* \* \*